United States Patent
Thompson

(10) Patent No.: US 12,331,323 B1
(45) Date of Patent: Jun. 17, 2025

(54) COMPOSITION FOR REGULATING PRODUCTION OF FUSION PROTEINS

(71) Applicant: ERAD Therapeutics Canada Inc., Caledon (CA)

(72) Inventor: Bradley G. Thompson, Calgary (CA)

(73) Assignee: ERAD Therapeutics Canada Inc., Caledon (CA)

(*) Notice: Subject to any disclaimer, the term of this patent is extended or adjusted under 35 U.S.C. 154(b) by 0 days.

(21) Appl. No.: 18/885,902

(22) Filed: Sep. 16, 2024

(51) Int. Cl.
| | |
|---|---|
| *C12N 15/86* | (2006.01) |
| *C07K 14/28* | (2006.01) |
| *C12N 7/00* | (2006.01) |
| *C12N 15/33* | (2006.01) |
| *C12N 15/864* | (2006.01) |

(52) U.S. Cl.
CPC .............. *C12N 7/00* (2013.01); *C07K 14/28* (2013.01); *C12N 2750/14122* (2013.01); *C12N 2750/14143* (2013.01)

(58) Field of Classification Search
None
See application file for complete search history.

(56) References Cited

FOREIGN PATENT DOCUMENTS

WO   WO-2011025905 A1 *  3/2011  ......... A61K 38/2228

OTHER PUBLICATIONS

Bharati and Ganguly, Cholera toxin: A paradigm of a multifunctional protein, Indian J Med Res 133, Feb. 2011, pp. 179-187.*
Arrington et al, Plasmid Vectors Encoding Cholera Toxin or the Heat-Labile Enterotoxin from *Escherichia coli* are Strong Adjuvants for DNA Vaccines, Journal of Virology, May 2002, p. 4536-4546.*

* cited by examiner

*Primary Examiner* — Maria Marvich
(74) *Attorney, Agent, or Firm* — Lathrop GPM LLP; Brian C. Trinque; Christine Greene

(57) ABSTRACT

Some embodiments of the present disclosure relate to one or more compositions that upregulate the production of one or more sequences of mRNA. The sequences of mRNA may encode for translation of target biomolecules, thereby causing an increase in bioavailability of the target biomolecules within a subject that is administered the one or more compositions. In some embodiments of the present disclosure, the target biomolecules are modified Cholera toxin A and Cholera toxin B.

4 Claims, No Drawings

**Specification includes a

COMPOSITION FOR REGULATING PRODUCTION OF FUSION PROTEINS

SEQUENCE LISTING

The present application is being filed along with a Sequence Listing in computer readable format. The Sequence Listing is provided as a file entitled 757778 AS FILED Sequence Listing.xml created Oct. 23, 2024, and is approximately 17.442 bytes in size. The information in the computer readable format of the sequence listing is incorporated herein by reference in its entirety.

TECHNICAL FIELD

The present disclosure generally relates to compositions for regulating the production of proteins. In particular, the present disclosure relates to compositions for regulating gene expression and, consequently, the production of modified Cholera toxin A and Cholera toxin B.

BACKGROUND

Proteins with a single amino acid mutation, or mutations at more than one amino acid, will generally not fold into fully functional proteins.

Misfolded proteins are degraded by the endoplasmic reticulum.

These misfolded proteins may retain some of their function. As such, it may be desirable to establish therapies, treatments and/or interventions that may result from interfering with endoplasmic reticulum mediated protein degradation.

Modified Cholera toxin B in combination with Cholera toxin A has been demonstrated to interfere with endoplasmic reticulum mediated protein degradation.

SUMMARY

Some embodiments of the present disclosure relate to one or more compositions that upregulate the production of one or more sequences of mRNA. The sequences of mRNA may encode for translation of target biomolecules, thereby causing an increase in bioavailability of the target biomolecules within a subject that is administered the one or more compositions. In some embodiments of the present disclosure, the target biomolecules are modified Cholera toxin A and Cholera toxin B.

In some embodiments of the present disclosure the compositions comprise a plasmid of deoxyribonucleic acid (DNA) that includes one or more insert sequences of nucleotides that encode for the production of mRNA and a backbone sequence of nucleotides that facilitates introduction of the one or more insert sequences into one or more of a subject's cells where it is expressed and/or replicated. Expression of the one or more insert sequences by one or more cells of the subject results in an increased production of the mRNA and, consequently, increased translation of the target biomolecules by one or more of the subject's cells.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding an mRNA sequence that encodes for modified Cholera toxin A and Cholera toxin B.

Some embodiments of the present disclosure relate to a method of making a composition/target cell complex. The method comprising a step of administering an RP comprising SEQ ID NO. 1 and SEQ ID NO. 2 to a target cell for forming the composition/target cell complex, wherein the composition/target cell complex causes the target cell to increase production of one or more sequences of mRNA that increases production of the target biomolecules.

Embodiments of the present disclosure relate to at least one approach for inducing endogenous production of one or more sequences of mRNA that encodes for target biomolecules, for example modified Cholera toxin A and Cholera toxin B. A first approach utilizes gene vectors containing nucleotide sequences for increasing the endogenous production of one or more sequences of mRNA, which are complete or partial sequences of modified Cholera toxin A and Cholera toxin B and/or combinations thereof, which can be administered to a subject to increase the subject's production of one or more sequences of the mRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the production by one or more target cells of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecules" refers to modified Cholera toxin A and Cholera toxin B.

As used therein, the term "target cell" refers to one or more cells and/or cell types that are affected, either directly or indirectly, by a biomolecule.

As used therein, the term “therapeutically effective amount” refers to the amount of the composition used that is of sufficient quantity to ameliorate, treat and/or inhibit one or more of a disease, disorder or a symptom thereof. The “therapeutically effective amount” will vary depending on the composition used, the route of administration of the composition and the severity of the disease, disorder or symptom thereof. The subject’s age, weight and genetic make-up may also influence the amount of the composition that will be a therapeutically effective amount.

As used therein, the terms “treat”, “treatment” and “treating” refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term “treatment” refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms “unit dosage form” and “unit dose” refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered by a viral vector. In some embodiments of the present disclosure, the vector is an adeno-associated virus vector.

In some embodiments of the present disclosure, the insert comprises one or more nucleotide sequences that encode for production of at least one sequence of mRNA that increases the production of target biomolecules, such as modified Cholera toxin A and Cholera toxin B.

In some embodiments of the present disclosure, the target biomolecules are Cholera toxin A and Cholera toxin B.

In some embodiments of the present disclosure, the subject may respond to receiving a therapeutic amount of the composition by changing production and/or functionality of one or more i molecules by changing production of one or more DNA sequences, one or more RNA sequences, and/or one or more proteins that regulate the levels and/or functionality of the one or more intermediary molecules.

In some embodiments of the present disclosure, administering a therapeutic amount of the composition to a subject upregulates the production, functionality or both of one or more sequences of mRNA that each encode for one or more biomolecules.

In some embodiments of the present disclosure, the composition is an RP that may be used for gene therapy. The gene therapy is useful for increasing the subject’s endogenous production of one or more sequences of mRNA that encode for target biomolecules. For example, the RP can contain one or more nucleotide sequences that cause increased production of one or more nucleotide sequences that cause an increased production of one or more mRNA sequences that encode for biomolecules, such as modified Cholera toxin A and Cholera toxin B.

In some embodiments of the present disclosure, the delivery vehicle of the RP used for gene therapy may be a vector that comprises a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ $TCID_{50}$/kg (50% tissue culture infective dose per kilogram of the patient’s body mass). In some embodiments of the present disclosure, the therapeutically effective amount of the composition that is administered to the patient is about $1\times10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1\times10^{16}$ TCP/kg.

Some embodiments of the present disclosure relate to an adeno-associated virus (AAV) genome consisting of an RP that, when operable inside a target cell, will cause the target cell to produce an mRNA sequence that upregulates production of biomolecules, with examples being modified Cholera toxin A and Cholera toxin B. The RP is comprised of AAV2 inverted terminal repeats (ITRs), a composite CASI promoter, and a human growth hormone (HGH) signal peptide, followed by a mRNA expression cassette encoding for modified Cholera toxin A and Cholera toxin B, followed by a Woodchuck Hepatitis Virus post-transcriptional regulatory element (WPRE) and a Simian virus 40 (SV40) polyadenylation (polyA) signal.

```
SEQ ID NO. 1(backbone sequence No. 1):
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAG

GAGTTGTGGCCCGTTGTCAGGCAACGTGGCGTGGTGTGCACTGTGTTTGCTGACGCA

ACCCCCACTGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGCTGCTGGA

CAGGGGCTCGGCTGTTGGGCACTGACAATTCCGTGGTGTTGTCGGGGAAATCATCGT

CCTTTCCTTGGCTGCTCGCCTGTGTTGCCACCTGGATTCTGCGCGGGACGTCCTTCTG

CTACGTCCCTTCGGCCCTCAATCCAGCGGACCTTCCTTCCCGCGGCCTGCTGCCGGCT

CTGCGGCCTCTTCCGCGTCTTCGCCTTCGCCCTCAGACGAGTCGGATCTCCCTTTGGG

CCGCCTCCCCGCCTAAGCTTATCGATACCGTCGAGATCTAACTTGTTTATTGCAGCTT

ATAATGGTTACAAATAAAGCAATAGCATCACAAATTTCACAAATAAAGCATTTTTTT

CACTGCATTCTAGTTGTGGTTTGTCCAAACTCATCAATGTATCTTATCATGTCTGGAT

CTCGACCTCGACTAGAGCATGGCTACGTAGATAAGTAGCATGGCGGGTTAATCATTA

ACTACAAGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGGCGGCC

TCAGTGAGCGAGCGAGCGCGCCAGCTGGCGTAATAGCGAAGAGGCCCGCACCGATC

GCCCTTCCCAACAGTTGCGCAGCCTGAATGGCGAATGGAATTCCAGACGATTGAGC

GTCAAAATGTAGGTATTTCCATGAGCGTTTTTCCTGTTGCAATGGCTGGCGGTAATA

TTGTTCTGGATATTACCAGCAAGGCCGATAGTTTGAGTTCTTCTACTCAGGCAAGTG

ATGTTATTACTAATCAAAGAAGTATTGCGACAACGGTTAATTTGCGTGATGGACAGA

CTCTTTTACTCGGTGGCCTCACTGATTATAAAAACACTTCTCAGGATTCTGGCGTACC

GTTCCTGTCTAAAATCCCTTTAATCGGCCTCCTGTTTAGCTCCCGCTCTGATTCTAAC

GAGGAAAGCACGTTATACGTGCTCGTCAAAGCAACCATAGTACGCGCCCTGTAGCG

GCGCATTAAGCGCGGCGGGTGTGGTGGTTACGCGCAGCGTGACCGCTACACTTGCC

AGCGCCCTAGCGCCCGCTCCTTTCGCTTTCTTCCCTTCCTTTCTCGCCACGTTCGCCG

GCTTTCCCCGTCAAGCTCTAAATCGGGGGCTCCCTTTAGGGTTCCGATTTAGTGCTTT

ACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGA

CTCTTGTTCCAAACTGGAACAACACTCAACCCTATCTCGGTCTATTCTTTTGATTTAT

AAGGGATTTTGCCGATTTCGGCCTATTGGTTAAAAAATGAGCTGATTTAACAAAAAT

TTAACGCGAATTTTAACAAAATATTAACGTTTACAATTTAAATATTTGCTTATACAAT

CTTCCTGTTTTTGGGGCTTTTCTGATTATCAACCGGGGTACATATGATTGACATGCTA
```

-continued

```
GTTTTACGATTACCGTTCATCGATTCTCTTGTTTGCTCCAGACTCTCAGGCAATGACC
TGATAGCCTTTGTAGAGACCTCTCAAAAATAGCTACCCTCTCCGGCATGAATTTATC
AGCTAGAACGGTTGAATATCATATTGATGGTGATTTGACTGTCTCCGGCCTTTCTCAC
CCGTTTGAATCTTTACCTACACATTACTCAGGCATTGCATTTAAAATATATGAGGGTT
CTAAAAATTTTTATCCTTGCGTTGAAATAAAGGCTTCTCCCGCAAAAGTATTACAGG
GTCATAATGTTTTGGTACAACCGATTTAGCTTTATGCTCTGAGGCTTTATTGCTTAA
TTTTGCTAATTCTTTGCCTTGCCTGTATGATTTATTGGATGTTGGAATTCCTGATGCG
GTATTTTCTCCTTACGCATCTGTGCGGTATTTCACACCGCATATGGTGCACTCTCAGT
ACAATCTGCTCTGATGCCGCATAGTTAAGCCAGCCCCGACACCCGCCAACACCCGCT
GACGCGCCCTGACGGGCTTGTCTGCTCCCGGCATCCGCTTACAGACAAGCTGTGACC
GTCTCCGGGAGCTGCATGTGTCAGAGGTTTTCACCGTCATCACCGAAACGCGCGAGA
CGAAAGGGCCTCGTGATACGCCTATTTTTATAGGTTAATGTCATGATAATAATGGTT
TCTTAGACGTCAGGTGGCACTTTTCGGGGAAATGTGCGCGGAACCCCTATTTGTTTA
TTTTTCTAAATACATTCAAATATGTATCCGCTCATGAGACAATAACCCTGATAAATG
CTTCAATAATATTGAAAAAGGAAGAGTATGAGTATTCAACATTTCCGTGTCGCCCTT
ATTCCCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAACTGGAT
CTCAACAGCGGTAAGATCCTTGAGAGTTTTCGCCCCGAAGAACGTTTTCCAATGATG
AGCACTTTTAAAGTTCTGCTATGTGGCGCGGTATTATCCCGTATTGACGCCGGGCAA
GAGCAACTCGGTCGCCGCATACACTATTCTCAGAATGACTTGGTTGAGTACTCACCA
GTCACAGAAAAGCATCTTACGGATGGCATGACAGTAAGAGAATTATGCAGTGCTGC
CATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATC
GTTGGGAACCGGAGCTGAATGAAGCCATACCAAACGACGAGCGTGACACCACGATG
CCTGTAGCAATGGCAACAACGTTGCGCAAACTATTAACTGGCGAACTACTTACTCTA
GCTTCCCGGCAACAATTAATAGACTGGATGGAGGCGGATAAAGTTGCAGGACCACT
TCTGCGCTCGGCCCTTCCGGCTGGCTGGTTTATTGCTGATAAATCTGGAGCCGGTGA
GCGTGGGTCTCGCGGTATCATTGCAGCACTGGGGCCAGATGGTAAGCCCTCCCGTAT
CGTAGTTATCTACACGACGGGGAGTCAGGCAACTATGGATGAACGAAATAGACAGA
TCGCTGAGATAGGTGCCTCACTGATTAAGCATTGGTAACTGTCAGACCAAGTTTACT
CATATATACTTTAGATTGATTTAAAACTTCATTTTTAATTTAAAAGGATCTAGGTGAA
GATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTA
GCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCA
GCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGAGCGCA
```

-continued

```
CGAGGGAGCTTCCAGGGGAAACGCCTGGTATCTTTATAGTCCTGTCGGGTTTCGCC

ACCTCTGACTTGAGCGTCGATTTTTGTGATGCTCGTCAGGGGGGCGGAGCCTATGGA

AAAACGCCAGCAACGCGGCCTTTTTACGGTTCCTGGCCTTTTGCTGGCCTTTTGCTCA

CATGTTCTTTCCTGCGTTATCCCCTGATTCTGTGGATAACCGTATTACCGCCTTTGAG

TGAGCTGATACCGCTCGCCGCAGCCGAACGACCGAGCGCAGCGAGTCAGTGAGCGA

GGAAGCGGAAGAGCGCCCAATACGCAAACCGCCTCTCCCCGCGCGTTGGCCGATTC

ATTAATGCAGCAGCTGCGCGCTCGCTCGCTCACTGAGGCCGCCCGGGCAAAGCCCG

GGCGTCGGGCGACCTTTGGTCGCCCGGCCTCAGTGAGCGAGCGAGCGCGCAGAGAG

GGAGTGGCCAACTCCATCACTAGGGGTTCCTTGTAGTTAATGATTAACCCGCCATGC

TACTTATCTACGTAGCCATGCTCTAGGACATTGATTATTGACTAGTGGAGTTCCGCGT

TACATAACTTACGGTAAATGGCCCGCCTGGCTGACCGCCCAACGACCCCCGCCCATT

GACGTCAATAATGACGTATGTTCCCATAGTAACGCCAATAGGGACTTTCCATTGACG

TCAATGGGTGGAGTATTTACGGTAAACTGCCCACTTGGCAGTACATCAAGTGTATCA

TATGCCAAGTACGCCCCCTATTGACGTCAATGACGGTAAATGGCCCGCCTGGCATTA

TGCCCAGTACATGACCTTATGGGACTTTCCTACTTGGCAGTACATCTACGTATTAGTC

ATCGCTATTACCATGGTCGAGGTGAGCCCCACGTTCTGCTTCACTCTCCCCATCTCCC

CCCCCTCCCCACCCCCAATTTTGTATTTATTTATTTTTTAATTATTTTGTGCAGCGATG

GGGGGGGGGGGGGGGGGGCGCGCGCCAGGCGGGGGGGGGCGGGGCGAGGGGC

GGGGCGGGGCGAGGCGGAGAGGTGCGGCGGCAGCCAATCAGAGCGGCGCGCTCCG

AAAGTTTCCTTTTATGGCGAGGCGGCGGCGGCGGCGGCCCTATAAAAAGCGAAGCG

CGCGGCGGGCGGGAGTCGCTGCGCGCTGCCTTCGCCCCGTGCCCCGCTCCGCCGCCG

CCTCGCGCCGCCCGCCCCGGCTCTGACTGACCGCGTTACTAAAACAGGTAAGTCCGG

CCTCCGCGCCGGGTTTTGGCGCCTCCCGCGGGCGCCCCCCTCCTCACGGCGAGCGCT

GCCACGTCAGACGAAGGGCGCAGCGAGCGTCCTGATCCTTCCGCCCGGACGCTCAG

GACAGCGGCCCGCTGCTCATAAGACTCGGCCTTAGAACCCCAGTATCAGCAGAAGG

ACATTTTAGGACGGGACTTGGGTGACTCTAGGGCACTGGTTTTCTTTCCAGAGAGCG

GAACAGGCGAGGAAAAGTAGTCCCTTCTCGGCGATTCTGCGGAGGGATCTCCGTGG

GGCGGTGAACGCCGATGATGCCTCTACTAACCATGTTCATGTTTTCTTTTTTTTCTA

CAGGTCCTGGGTGACGAACAGGGTACCGCCACC 3'
```

SEQ ID NO. 2 (mRNA expression cassette No. 2 - modified
Cholera toxin A and Cholera toxin B):
```
5' AACGATGATAAACTGTATCGCGCGGATAGCCGCCCGCCGGATGAAATTAAACAGAG

CGGCGGCCTGATGCCGCGCGGCCAGAGCGAATATTTTGATCGCGGCACCCAGATGA

ACATTAACCTGTATGATCATGCGCGCGGCACCCAGACCGGCTTTGTGCGCCATGATG

ATGGCTATGTGAGCACCAAAATTAGCCTGCGCAGCGCGCATCTGGTGGGCCAGACC

ATTCTGAGCGGCCATAGCACCTATTATATTTATGTGATTGCGACCGCGCCGAACATG

TTTAACGTGAACGATGTGCTGGGCGCGTATAGCAGCCATCCGGATGAACAGGAAGT

GAGCGCGCTGGGCGGCATTCCGTATAGCCAGATTTATGGCTGGTATCGCGTGCATTT

TGGCGTGCTGGATGAACAGCTGCATCGCAACCGCGGCTATCGCGATCGCTATTATAG

CAACCTGGATATTGCGCCGGCGGCGGATGGCTATGGCCTGGCGGGCTTTCCGCCGG

AACATCGCGCGTGGCGCGAAGAACCGTGGATTCATCATGCGCCGCCGGGCTGCGGC
```

-continued

```
AACGCGCCGCGCAGCAGCATGAGCAACACCTGCGATGAAAAAACCCAGAGCCTGG

GCGTGAAATTTCTGGATGAATATCAGAGCAAAGTGAAACGCCAGATTTTTAGCGGCT

ATCAGAGCGATATTGATACCCATAACCGCATTAAAGATGAACTGATGGCAACAGGG

AGCCGAACCTCTCTGCTCCTTGCTTTCGGGCTCCTTTGCCTACCGTGGCTCCAAGAGG

GCTCGGCAACCCCGCAGAACATTACCGATCTGTGCGCGGAATATCATAACACCCAG

ATTCATACCCTGAACGATAAAATTTTTAGCTATACCGAAAGCCTGGCGGGCAAACGC

GAAATGGCGATTATTACCTTTAAAAACGGCGCGACCTTTCAGGTGGAAGTGCCGGG

CAGCCAGCATATTGATAGCCAGAAAAAAGCGATTGAACGCATGAAAGATACCCTGC

GCATTGCGTATCTGACCGAAGCGAAAGTGGAAAAACTGTGCGTGTGGAACAACAAA

ACCCCGCATGCGATTGCGGCGATTAGCATGGCGAACTCTAGAGAT 3'
```

SEQ ID NO. 3 = SEQ ID NO. 1 + SEQ ID NO. 2

```
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAG

GAGTTGTGGCCCGTTGTCAGGCAACGTGGCGTGGTGTGCACTGTGTTTGCTGACGCA

ACCCCCACTGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGCTGCTGGA

CAGGGGCTCGGCTGTTGGGCACTGACAATTCCGTGGTGTTGTCGGGGAAATCATCGT

CCTTTCCTTGGCTGCTCGCCTGTGTTGCCACCTGGATTCTGCGCGGGACGTCCTTCTG

CTACGTCCCTTCGGCCCTCAATCCAGCGGACCTTCCTTCCCGCGGCCTGCTGCCGGCT

CTGCGGCCTCTTCCGCGTCTTCGCCTTCGCCCTCAGACGAGTCGGATCTCCCTTTGGG

CCGCCTCCCCGCCTAAGCTTATCGATACCGTCGAGATCTAACTTGTTTATTGCAGCTT

ATAATGGTTACAAATAAAGCAATAGCATCACAAATTTCACAAATAAAGCATTTTTTT

CACTGCATTCTAGTTGTGGTTTGTCCAAACTCATCAATGTATCTTATCATGTCTGGAT

CTCGACCTCGACTAGAGCATGGCTACGTAGATAAGTAGCATGGCGGGTTAATCATTA

ACTACAAGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGGCGGCC

TCAGTGAGCGAGCGAGCGCGCCAGCTGGCGTAATAGCGAAGAGGCCCGCACCGATC

GCCCTTCCCAACAGTTGCGCAGCCTGAATGGCGAATGGAATTCCAGACGATTGAGC

GTCAAAATGTAGGTATTTCCATGAGCGTTTTTCCTGTTGCAATGGCTGGCGGTAATA

TTGTTCTGGATATTACCAGCAAGGCCGATAGTTTGAGTTCTTCTACTCAGGCAAGTG

ATGTTATTACTAATCAAAGAAGTATTGCGACAACGGTTAATTTGCGTGATGGACAGA

CTCTTTTACTCGGTGGCCTCACTGATTATAAAAACACTTCTCAGGATTCTGGCGTACC

GTTCCTGTCTAAAATCCCTTTAATCGGCCTCCTGTTTAGCTCCCGCTCTGATTCTAAC

GAGGAAAGCACGTTATACGTGCTCGTCAAAGCAACCATAGTACGCGCCCTGTAGCG

GCGCATTAAGCGCGGCGGGTGTGGTGGTTACGCGCAGCGTGACCGCTACACTTGCC

AGCGCCCTAGCGCCCGCTCCTTTCGCTTTCTTCCCTTCCTTTCTCGCCACGTTCGCCG

GCTTTCCCCGTCAAGCTCTAAATCGGGGGCTCCCTTTAGGGTTCCGATTTAGTGCTTT

ACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGA

CTCTTGTTCCAAACTGGAACAACACTCAACCCTATCTCGGTCTATTCTTTTGATTTAT
```

-continued
```
AAGGGATTTTGCCGATTTCGGCCTATTGGTTAAAAAATGAGCTGATTTAACAAAAAT
TTAACGCGAATTTTAACAAAATATTAACGTTTACAATTTAAATATTTGCTTATACAAT
CTTCCTGTTTTTGGGGCTTTTCTGATTATCAACCGGGGTACATATGATTGACATGCTA
GTTTTACGATTACCGTTCATCGATTCTCTTGTTTGCTCCAGACTCTCAGGCAATGACC
TGATAGCCTTTGTAGAGACCTCTCAAAAATAGCTACCCTCTCCGGCATGAATTTATC
AGCTAGAACGGTTGAATATCATATTGATGGTGATTTGACTGTCTCCGGCCTTTCTCAC
CCGTTTGAATCTTTACCTACACATTACTCAGGCATTGCATTTAAAATATATGAGGGTT
CTAAAAATTTTTATCCTTGCGTTGAAATAAAGGCTTCTCCCGCAAAAGTATTACAGG
GTCATAATGTTTTTGGTACAACCGATTTAGCTTTATGCTCTGAGGCTTTATTGCTTAA
TTTTGCTAATTCTTTGCCTTGCCTGTATGATTTATTGGATGTTGGAATTCCTGATGCG
GTATTTTCTCCTTACGCATCTGTGCGGTATTTCACACCGCATATGGTGCACTCTCAGT
ACAATCTGCTCTGATGCCGCATAGTTAAGCCAGCCCCGACACCCGCCAACACCCGCT
GACGCGCCCTGACGGGCTTGTCTGCTCCCGGCATCCGCTTACAGACAAGCTGTGACC
GTCTCCGGGAGCTGCATGTGTCAGAGGTTTTCACCGTCATCACCGAAACGCGCGAGA
CGAAAGGGCCTCGTGATACGCCTATTTTTATAGGTTAATGTCATGATAATAATGGTT
TCTTAGACGTCAGGTGGCACTTTTCGGGGAAATGTGCGCGGAACCCCTATTTGTTTA
TTTTTCTAAATACATTCAAATATGTATCCGCTCATGAGACAATAACCCTGATAAATG
CTTCAATAATATTGAAAAAGGAAGAGTATGAGTATTCAACATTTCCGTGTCGCCCTT
ATTCCCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAACTGGAT
CTCAACAGCGGTAAGATCCTTGAGAGTTTTCGCCCCGAAGAACGTTTTCCAATGATG
AGCACTTTTAAAGTTCTGCTATGTGGCGCGGTATTATCCCGTATTGACGCCGGGCAA
GAGCAACTCGGTCGCCGCATACACTATTCTCAGAATGACTTGGTTGAGTACTCACCA
GTCACAGAAAAGCATCTTACGGATGGCATGACAGTAAGAGAATTATGCAGTGCTGC
CATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATC
GTTGGGAACCGGAGCTGAATGAAGCCATACCAAACGACGAGCGTGACACCACGATG
CCTGTAGCAATGGCAACAACGTTGCGCAAACTATTAACTGGCGAACTACTTACTCTA
GCTTCCCGGCAACAATTAATAGACTGGATGGAGGCGGATAAAGTTGCAGGACCACT
TCTGCGCTCGGCCCTTCCGGCTGGCTGGTTTATTGCTGATAAATCTGGAGCCGGTGA
GCGTGGGTCTCGCGGTATCATTGCAGCACTGGGGCCAGATGGTAAGCCCTCCCGTAT
CGTAGTTATCTACACGACGGGGAGTCAGGCAACTATGGATGAACGAAATAGACAGA
TCGCTGAGATAGGTGCCTCACTGATTAAGCATTGGTAACTGTCAGACCAAGTTTACT
CATATATACTTTAGATTGATTTAAAACTTCATTTTTAATTTAAAAGGATCTAGGTGAA
GATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTA
GCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCA
```

-continued

```
GCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGAGCGCA
CGAGGGAGCTTCCAGGGGAAACGCCTGGTATCTTTATAGTCCTGTCGGGTTTCGCC
ACCTCTGACTTGAGCGTCGATTTTTGTGATGCTCGTCAGGGGGGCGGAGCCTATGGA
AAAACGCCAGCAACGCGGCCTTTTTACGGTTCCTGGCCTTTTGCTGGCCTTTTGCTCA
CATGTTCTTTCCTGCGTTATCCCCTGATTCTGTGGATAACCGTATTACCGCCTTTGAG
TGAGCTGATACCGCTCGCCGCAGCCGAACGACCGAGCGCAGCGAGTCAGTGAGCGA
GGAAGCGGAAGAGCGCCCAATACGCAAACCGCCTCTCCCCGCGCGTTGGCCGATTC
ATTAATGCAGCAGCTGCGCGCTCGCTCGCTCACTGAGGCCGCCCGGGCAAAGCCCG
GGCGTCGGGCGACCTTTGGTCGCCCGGCCTCAGTGAGCGAGCGAGCGCGCAGAGAG
GGAGTGGCCAACTCCATCACTAGGGGTTCCTTGTAGTTAATGATTAACCCGCCATGC
TACTTATCTACGTAGCCATGCTCTAGGACATTGATTATTGACTAGTGGAGTTCCGCGT
TACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACG
TCAATGGGTGGAGTATTTACGGTAAACTGCCCACTTGGCAGTACATCAAGTGTATCA
TATGCCAAGTACGCCCCCTATTGACGTCAATGACGGTAAATGGCCCGCCTGGCATTA
TGCCCAGTACATGACCTTATGGGACTTTCCTACTTGGCAGTACATCTACGTATTAGTC
ATCGCTATTACCATGGTCGAGGTGAGCCCCACGTTCTGCTTCACTCTCCCCATCTCCC
CCCCCTCCCCACCCCCAATTTTGTATTTATTTATTTTTTAATTATTTTGTGCAGCGATG
GGGGGGGGGGGGGGGGGGCGCGCGCCAGGCGGGGCGGGGCGGGGCGAGGGGC
GGGGCGGGGCGAGGCGGAGAGGTGCGGCGGCAGCCAATCAGAGCGGCGCGCTCCG
AAAGTTTCCTTTTATGGCGAGGCGGCGGCGGCGGCGGCCCTATAAAAAGCGAAGCG
CGCGGCGGGGGAGTCGCTGCGCGCTGCCTTCGCCCCGTGCCCCGCTCCGCCGCCG
CCTCGCGCCGCCCGCCCCGGCTCTGACTGACCGCGTTACTAAAACAGGTAAGTCCGG
CCTCCGCGCCGGGTTTTGGCGCCTCCCGCGGGCGCCCCCCTCCTCACGGCGAGCGCT
GCCACGTCAGACGAAGGGCGCAGCGAGCGTCCTGATCCTTCCGCCCGGACGCTCAG
GACAGCGGCCCGCTGCTCATAAGACTCGGCCTTAGAACCCCAGTATCAGCAGAAGG
ACATTTTAGGACGGGACTTGGGTGACTCTAGGGCACTGGTTTTCTTTCCAGAGAGCG
GAACAGGCGAGGAAAAGTAGTCCCTTCTCGGCGATTCTGCGGAGGGATCTCCGTGG
GGCGGTGAACGCCGATGATGCCTCTACTAACCATGTTCATGTTTTCTTTTTTTTCTA
CAGGTCCTGGGTGACGAACAGGGTACCGCCACCAACGATGATAAACTGTATCGCGC
GGATAGCCGCCCGCCGGATGAAATTAAACAGAGCGGCGGCCTGATGCCGCGCGGCC
AGAGCGAATATTTTGATCGCGGCACCCAGATGAACATTAACCTGTATGATCATGCGC
GCGGCACCCAGACCGGCTTTGTGCGCCATGATGATGGCTATGTGAGCACCAAAATTA
GCCTGCGCAGCGCGCATCTGGTGGGCCAGACCATTCTGAGCGGCCATAGCACCTATT
ATATTTATGTGATTGCGACCGCGCCGAACATGTTTAACGTGAACGATGTGCTGGGCG
CGTATAGCAGCCATCCGGATGAACAGGAAGTGAGCGCGCTGGGCGGCATTCCGTAT
AGCCAGATTTATGGCTGGTATCGCGTGCATTTTGGCGTGCTGGATGAACAGCTGCAT
CGCAACCGCGGCTATCGCGATCGCTATTATAGCAACCTGGATATTGCGCCGGCGGCG
```

```
                                                -continued
GATGGCTATGGCCTGGCGGGCTTTCCGCCGGAACATCGCGCGTGGCGCGAAGAACC

GTGGATTCATCATGCGCCGCCGGGCTGCGGCAACGCGCCGCGCAGCAGCATGAGCA

ACACCTGCGATGAAAAAACCCAGAGCCTGGGCGTGAAATTTCTGGATGAATATCAG

AGCAAAGTGAAACGCCAGATTTTTAGCGGCTATCAGAGCGATATTGATACCCATAA

CCGCATTAAAGATGAACTGATGGCAACAGGGAGCCGAACCTCTCTGCTCCTTGCTTT

CGGGCTCCTTTGCCTACCGTGGCTCCAAGAGGGCTCGGCAACCCCGCAGAACATTAC

CGATCTGTGCGCGGAATATCATAACACCCAGATTCATACCCTGAACGATAAAATTTT

TAGCTATACCGAAAGCCTGGCGGGCAAACGCGAAATGGCGATTATTACCTTTAAAA

ACGGCGCGACCTTTCAGGTGGAAGTGCCGGGCAGCCAGCATATTGATAGCCAGAAA

AAAGCGATTGAACGCATGAAAGATACCCTGCGCATTGCGTATCTGACCGAAGCGAA

AGTGGAAAAACTGTGCGTGTGGAACAACAAAACCCCGCATGCGATTGCGGCGATTA

GCATGGCGAACTCTAGAGAT 3'
```

As will be appreciated by those skilled in the art, because the recombinant plasmid is a circular vector, the one or more sequences of the mRNA expression cassettes may be connected at the 3' end of SEQ ID NO. 1, as shown in SEQ ID NO. 3, or at the 5' end of SEQ ID NO. 1.

As will be appreciated by those skilled in the art, a perfect match of nucleotides with each of the miRNA expression cassette sequences is not necessary in order to have the desired result of increased bioavailability of the target biomolecule as a result of the target cell producing the mRNA sequence of the target biomolecule. In some embodiments of the present disclosure, about 80% to about 100% nucleotide sequence matching with each of the mRNA expression cassettes causes the desired result. In some embodiments of the present disclosure, about 85% to about 100% nucleotide sequence matching with each of the mRNA expression cassettes causes the desired result. In some embodiments of the present disclosure, about 90% to about 100% nucleotide sequence matching with each of the mRNA expression cassettes causes the desired result. In some embodiments of the present disclosure, about 95% to about 100% nucleotide sequence matching with each of the mRNA expression cassettes causes the desired result.

Example 1-Expression Cassette

Expression cassettes for expressing mRNA were synthesized. The synthesized mRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mRNA expression cassette was amplified by polymerase chain reaction (PCR) using Taq polymerase and the PCR products were gel purified. The bands of interest were also excised and purified using a gel extraction kit. These PCR products contained the mRNA expression cassettes in addition to 15 base pair 5' and 3' overhangs that aligned with the ends of the linearized pAVA-00200 backbone. Using in-fusion cloning, the amplified mRNA expression cassettes are integrated with the pAVA-00200 backbone via homologous recombination. The resulting RP contained the following: 5' ITR, CASI promoter, mRNA expression cassette, WPRE, SV40 polyA and ITR 3'.

The invention claimed is:

1. A composition that comprises a recombinant plasmid (RP) with a sequence of nucleotides that encodes a messenger ribonucleic acid (mRNA) sequence that encodes modified Cholera toxin A and Cholera toxin B, and wherein the sequence of nucleotides is about 95% to about 100% identical to the nucleotide sequence of SEQ ID NO: 2.

2. The composition of claim 1, wherein the RP is configured to be delivered to a target cell, wherein the RP is delivered by a viral vector.

3. The composition of claim 2, wherein the viral vector is an adeno associated virus (AAV).

4. A composition that comprises a RP with a sequence of nucleotides that encodes a mRNA sequence that encodes modified Cholera toxin A and Cholera toxin B, wherein the sequence of nucleotides is about 95% to about 100% identical to the nucleotide sequence of SEQ ID NO: 3.

* * * * *

SEQUENCE LISTING

```
Sequence total quantity: 3
SEQ ID NO: 1            moltype = DNA   length = 5852
FEATURE                 Location/Qualifiers
source                  1..5852
                        mol_type = other DNA
                        organism = Adeno-associated virus sp.
SEQUENCE: 1
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctctttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt cccccctcct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
```

```
cgggctttgc cgggcggcc tcagtgagcg agcgagcgcg ccagctggcg taatagcgaa    960
gaggcccgca ccgatcgccc ttcccaacag ttgcgcagcc tgaatggcga atggaattcc   1020
agacgattga gcgtcaaaat gtaggtattt ccatgagcgt ttttcctgtt gcaatggctg   1080
gcggtaatat tgttctggat attaccagca aggccgatag tttgagttct tctactcagg   1140
caagtgatgt tattactaat caaagaagta ttgcgacaag gttaaatttg cgtgatggac   1200
agactctttt actcggtggc ctcactgatt ataaaaacac ttctcaggat tctggcgtac   1260
cgttcctgtc taaaatccct ttaatcggcc tcctgtttag ctcccgctct gattctaacg   1320
aggaaagcac gttatacgtg ctcgtcaaag caaccatagt acgcgccctg tagcggcgca   1380
ttaagcgcgg cgggtgtggt ggttacgcgc agcgtgaccg ctacacttgc cagcgcccta   1440
gcgcccgctc ctttcgcttt cttcccttcc tttctcgcca cgttcgccgg ctttccccgt   1500
caagctctaa atcgggggct ccctttaggg ttccgattta gtgctttacg gcacctcgac   1560
cccaaaaaac ttgattaggg tgatggttca cgtagtgggc catcgccctg atagacggtt   1620
tttcgccctt tgacgttgga gtccacgttc tttaatagtg gactcttgtt ccaaactgga   1680
acaacactca acccctatctc ggtctattct tttgatttat aagggatttt gccgatttcg   1740
gcctattggt taaaaaatga gctgatttaa caaaaattta acggaatttt taacaaaata   1800
ttaacgttta caatttaaat atttgcttat acaatcttcc tgttttttggg gcttttctga   1860
ttatcaaccg gggtacatat gattgacatg ctagttttac gattaccgtt catcgattct   1920
cttgttttgct ccagactctc aggcaatgac ctgatagcct ttgtagagac ctctcaaaaa   1980
tagctaccct ctccggcatg aatttatcag ctagaacggt tgaatatcat attgatggtg   2040
atttgactgt ctccggcctt tctcacccgt ttgaatcttt acctacacat tactcaggca   2100
ttgcatttaa aatatgtgag ggttctaaaa atttttatcc ttgcgttgaa ataaaggctt   2160
ctcccgcaaa agtattacag ggtcataatg ttttttggtac aaccgattta gctttatgct   2220
ctgaggcttt attgcttaat tttgctaatt ctttgccttg cctgtatgat ttattggatg   2280
ttggaattcc tgatgcggta ttttctcctt acgcatctgt gcggtatttc acaccgcata   2340
tggtgcactc tcagtacaat ctgctctgat gccgcatagt taagccagcc ccgacacccg   2400
ccaacacccg ctgacgcgcc ctgacgggct tgtctgctcc cggcatccgc ttacagacaa   2460
gctgtgaccg tctccgggag ctgcatgtgt cagaggtttt caccgtcatc accgaaacgc   2520
gcgagacgaa agggcctcgt gatacgccta ttttttatagg ttaatgtcat gataataatg   2580
gtttcttaga cgtcaggtgg cacttttcgg ggaaatgtgc gcggaacccc tatttgttta   2640
tttttctaaa tacattcaaa tatgtatccg ctcatgagac aataacccctg ataaatgctt   2700
caataatatt gaaaaaggaa gagtatgagt attcaacatt tccgtgtcgc ccttattccc   2760
ttttttgcgg catttttgcct tcctgttttt gctcacccag aaacgctggt gaaagtaaaa   2820
gatgctgaag atcagttggg tgcacgagtg gttacatcg aactggatct caacagcggt   2880
aagatccttg agagttttcg ccccgaagaa cgttttccaa tgatgagcac ttttaaagtt   2940
ctgctatgtg gcgcggtatt atcccgtatt gacgccgggc aagagcaact cggtcgccgc   3000
atacactatt ctcagaatga cttggttgag tactcaccag tcacagaaaa gcatcttacg   3060
gatggcatga cagtaagaga attatgcagt gctgccataa ccatgagtga taacactgcg   3120
gccaacttac ttctgacaac gatcggagga ccgaaggagc taaccgcttt tttgcacaac   3180
atgggggatc atgtaactcg ccttgatcgt tgggaaccgg agctgaatga agccatacca   3240
aacgacgagc gtgacaccac gatgcctgta gcaatggcaa caacgttgcg caaactatta   3300
actggcgaac tacttactct agcttcccgg caacaattaa tagactggat ggaggcggat   3360
aaagttgcag gaccacttct gcgctcggcc cttccggctg gctggtttat tgctgataaa   3420
tctggagccg gtgagcgtgg gtctcgcggt atcattgcag cactggggcc agatggtaag   3480
ccctcccgta tcgtagttat ctacacgacg gggagtcagg caactatgga tgaacgaaat   3540
agacagatcg ctgagatagg tgcctcactg attaagcatt ggtaactgtc agaccaagtt   3600
tactcatata ctttttagat tgatttaaaa cttcattttt aatttaaaag gatctaggtg   3660
aagatccttt ttgataatct catgaccaaa atcccttaac gtgagttttc gttccactga   3720
gcgtcagacc ccgtagaaaa gatcaaagga tcttcttgag atcctttttt tctgcgcgta   3780
atctgctgct tgcaaacaaa aaaaccaccg ctaccagcgg tggtttgttt gccggatcaa   3840
gagctaccaa ctctttttcc gaaggtaact ggcttcagca gagcgcagat accaaatact   3900
gtccttctag tgtagccgta gttaggccac cacttcaaga actctgtagc accgcctaca   3960
tacctcgctc tgctaatcct gttaccagtg gctgctgcca gtggcgataa gtcgtgtctt   4020
accgggttgg actcaagacg atagttaccg gataaggcgc agcggtcggg ctgaacgggg   4080
ggttcgtgca cacagcccag cttggagcga acgacctaca ccgaactgag atacctacag   4140
cgtgagctat gagaaagcgc cacgcttccc gaagggagaa aggcggacag gtatccggta   4200
agcggcaggg tcggaacagg agagcgcacg agggagcttc caggggggaaa cgcctggtat   4260
ctttatagtc ctgtcgggtt tcgccacctc tgacttgagc gtcgattttt gtgatgctcg   4320
tcagggggcg gagcctatg gaaaaacgcc agcaacgcgg cctttttacg gttcctggcc   4380
ttttgctggc cttttgctca catgttcttt cctgcgttat cccctgattc tgtggataac   4440
cgtattaccg cctttgagtg agctgatacc gctcgccgca gccgaacgac cgagcgcagc   4500
gagtcagtga gcgaggaagc ggaagagcgc ccaatacgca aaccgcctct ccccgcgcgt   4560
tggccgattc attaatgcag cagctgcgcg ctcgctcgct cactgaggcc gcccgggcaa   4620
agcccggggc tcgggcgacc tttggtcgcc cggcctcagt gagcgagcga gcgcgcagag   4680
agggagtggc caactccatc actaggggtt ccttgtagtt aatgattaac cctgcatgct   4740
acttatctac gtagccatgc tctaggacat tgattattga ctagtggagt tccgcgttac   4800
ataacttacg gtaaatggcc cgcctggctg accgcccaac gacccccgcc cattgacgtc   4860
aataatgacg tatgttccca tagtaacgcc aatagggact ttccattgac gtcaatgggt   4920
ggagtattta cggtaaactg cccacttggc agtacatcaa gtgtatcata tgccaagtac   4980
gccccctatt gacgtcaatg acggtaaatg gcccgcctgg cattatgccc agtacatgac   5040
cttatgggac tttcctactt ggcagtacat ctacgtatta gtcatcgcta ttaccatggt   5100
cgaggtgagc cccacgttct gcttcactct ccccatctcc cccccctccc cacccccaat   5160
tttgtattta ttattttttt aattattttg tgcagcgatg ggggcggggg ggggggggg   5220
cgcgcgccag gcggggcggg gcgggcgag gggcggggcg gggcgaggcg gagaggtgcg   5280
gcgcagcca atcagagcgg cgcgctccga aagtttcctt ttatgcggag gcggcggcgg   5340
cggcggccct ataaaagcg aagcgcgcgg cgggcgggag tcgctgcgcg ctgccttcgc   5400
cccgtgcccc gctccgccgc cgcctcgcgc cgcccgcccc ggctctgact gaccgcgtta   5460
ctaaaacagg taagtccggc ctccgcgccg ggttttggcg cctcccgcgg gcgcccccct   5520
cctcacggcg agcgctgcca cgtcagacga agggcgcagc gagcgtcctg atccttccgc   5580
ccggacgctc aggacagcgg cccgctgctc ataagactcg gccttagaac cccagtatca   5640
```

```
gcagaaggac attttaggac gggacttggg tgactctagg gcactggttt tcttttccaga   5700
gagcggaaca ggcgaggaaa agtagtccct tctcggcgat tctgcggagg gatctccgtg   5760
gggcggtgaa cgccgatgat gcctctacta accatgttca tgttttcttt ttttttctac   5820
aggtcctggg tgacgaacag ggtaccgcca cc                                  5852

SEQ ID NO: 2           moltype = DNA  length = 1116
FEATURE                Location/Qualifiers
source                 1..1116
                       mol_type = other DNA
                       organism = Vibrio cholerae
SEQUENCE: 2
aacgatgata aactgtatcg cgcggatagc cgcccgccgg atgaaattaa acagagcggc     60
ggcctgatgc cgcgcggcca gagcgaatat tttgatcgcg gcacccagat gaacattaac    120
ctgtatgatc atgcgcgcgg cacccagacc ggctttgtgc gccatgatga tggctatgtg    180
agcaccaaaa ttagcctgcg cagcgcgcat ctggtgggcc agaccattct gagcggccat    240
agcacctatt atatttatgt gattgcgacc gcgccgaaca tgtttaacgt gaacgatgtg    300
ctgggcgcgt atagcagcca tccggatgaa caggaagtga gcgcgctggg cggcattccg    360
tatagccaga tttatggctg gtatcgcgtg cattttggcg tgctggatga acagctgcat    420
cgcaaccgcg gctatcgcga tcgctattat agcaacctgg atattgcgcc ggcggcggat    480
ggctatggcc tggcgggctt tccgccggaa catcgcgcgt ggcgcgaaga accgtggatt    540
catcatgcgc cgcggggctg cggcaacgcg ccgcgcagca gcatgagcaa cacctgcgat    600
gaaaaaaccc agagcctggg cgtgaaattt ctggatgaat atcagagcaa agtgaaacgc    660
cagatttttta gcggctatca gagcgatatt gatacccata accgcattaa agatgaactg    720
atggcaacag ggagccgaac ctctctgctc cttgctttcg ggctcctttg cctaccgtgg    780
ctccaagagg gctcggcaac cccgcagaac attaccgatc tgtgcgcgga atatcataac    840
acccagattc atacccctgaa cgataaaatt ttagctata ccgaaagcct ggcggggcaaa    900
cgcgaaatgg cgattattac ctttaaaaac ggcgcgacct ttcaggtgga agtgccgggc    960
agccagcata ttgatagcca gaaaaaagcg attgaacgca tgaaagatac cctgcgcatt   1020
gcgtatctga ccgaagcgaa agtggaaaaa ctgtgcgtgt ggaacaacaa aaccccgcat   1080
gcgattgcgg cgattagcat ggcgaactct agagat                             1116

SEQ ID NO: 3           moltype = DNA  length = 6968
FEATURE                Location/Qualifiers
source                 1..6968
                       mol_type = other DNA
                       organism = synthetic construct
SEQUENCE: 3
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttgggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc taagcttatc    600
gataccgtcg agatctaact tgtttattgc agcttataat ggttacaaat aaagcaatag    660
catcacaaat ttcacaaata agcatttttt tcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg ccagctgcg taatagcgaa    960
gaggcccgca ccgatcgccc ttcccaacag ttgcgcagcc tgaatggcga atggaattcc   1020
agacgattga gcgtcaaaat gtaggtattt ccatgagcgt ttttcctgtt gcaatggctg   1080
gcggtaatat tgttctggat attaccagca aggccgatag tttgagttct tctactcagg   1140
caagtgatgt tattactaat caaagaagta ttgcgacaac ggttaatttg cgtgatggac   1200
agactctttt actcggtggc ctcactgatt ataaaaacac ttctcaggat tctggcgtac   1260
cgttcctgtc taaaatccct ttaatcggcc tcctgttttag ctccgctc gattctaacg   1320
aggaaagcac gttatacgtg ctcgtcaaag caaccatagt acgcgccctg tagcggcgca   1380
ttaagcgcgg cgggtgtggt ggttacgcgc agcgtgaccg ctacacttgc cagcgcccta   1440
gcgcccgctc cttcgctttc ttcccttcc tttctcgcca cgttcgccgg ctttccccgt   1500
caagctctaa atcgggggct ccctttaggg ttccgattta gtgctttacg gcacctcgac   1560
cccaaaaaac ttgattaggg tgatggttca cgtagtgggc catcgccctg atagacggtt   1620
tttcgccctt tgacgttgga gtccacgttc tttaatagtg gactcttgtt ccaaactgga   1680
acaacactca accctatctc ggtctattct tttgatttat aagggatttt gccgatttcg   1740
gcctattggt taaaaaatga gctgatttaa caaaaattta cgcgaattt taacaaaata   1800
ttaacgttta caatttaaat atttgcttat acaatcttcc tgttttttggg gcttttctgc   1860
ttatcaaccg gggtacatat gattgcatg ctagtttac gattaccgtt catcgattct   1920
cttgtttgct ccagactctc aggcaatgac ctgatagcct ttgtagagac ctctcaaaaa   1980
tagctaccct ctccggcatg aatttatcag ctagaacggt tgaatatcat attgatggtg   2040
atttgactgt ctccggcctt tctcacccgt ttgaatcttt acctacacat tactcaggca   2100
ttgcatttaa aatatatgag ggttctaaaa atttttatcc ttgcgttgaa ataaaggctt   2160
ctcccgcaaa agtattacag gcatcataat gtttggtaca accgattta gctttatgct   2220
ctgaggcttt attgcttaat tttgctaatt ctttgccttg cctgtatgat ttattggatg   2280
ttggaattcc tgatgcggta ttttctcctt acgcatctgt gcggtatttc acaccgcata   2340
tggtgcactc tcagtacaat ctgctctgat gccgcatagt taagcagcc ccgacacccg   2400
ccaacacccg ctgacgcgcc ctgacgggct tgtctgctcc cggcatccgc ttacagacaa   2460
gctgtgaccg tctccgggag ctgcatgtgt cagaggtttt caccgtcatc accgaaacgc   2520
```

```
gcgagacgaa agggcctcgt gatacgccta tttttatagg ttaatgtcat gataataatg   2580
gtttcttaga cgtcaggtgg cacttttcgg ggaaatgtgc gcggaacccc tatttgttta   2640
tttttctaaa tacattcaaa tatgtatccg ctcatgagac aataaccctg ataaatgctt   2700
caataatatt gaaaaggaa gagtatgagt attcaacatt tccgtgtcgc ccttattccc    2760
tttttgcgg cattttgcct tcctgttttt gctcacccag aaacgctggt gaaagtaaaa   2820
gatgctgaag atcagttggg tgcacgagtg ggttacatcg aactggatct caacagcggt   2880
aagatccttg agagttttcg ccccgaagaa cgttttccaa tgatgagcac ttttaaagtt   2940
ctgctatgtg gcgcggtatt atcccgtatt gacgccggc aagagcaact cggtcgccgc    3000
atacactatt ctcagaatga cttggttgag tactcaccag tcacagaaaa gcatcttacg   3060
gatggcatga cagtaagaga attatgcagt gctgccataa ccatgagtga taacactgcg   3120
gccaacttac ttctgacaac gatcggagga ccgaaggagc taaccgcttt tttgcacaac   3180
atggggatc atgtaactcg ccttgatcgt tgggaaccgg agctgaatga agccatacca    3240
aacgacgagc gtgacaccac gatgcctgta gcaatggcaa caacgttgcg caaactatta   3300
actggcgaac tacttactct agcttcccgg caacaattaa tagactggat ggaggcggat   3360
aaagttgcag gaccacttct gcgctcggcc cttccggctg gctggtttat tgctgataaa   3420
tctggagccg gtgagcgtgg gtctcgcggt atcattgcag cactggggcc agatggtaag   3480
ccctcccgta tcgtagttat ctacacgacg gggagtcagg caactatgga tgaacgaaat   3540
agacagatcg ctgagatagg tgcctcactg attaagcatt ggtaactgtc agaccaagtt   3600
tactcatata tactttagat tgatttaaaa cttcatttt aatttaaaag gatctaggtg    3660
aagatccttt ttgataatct catgaccaaa atcccttaac gtgagttttc gttccactga   3720
gcgtcagacc ccgtagaaaa gatcaaagga tcttcttgag atccttttt tctgcgcgta    3780
atctgctgct tgcaaacaaa aaaccaccg ctaccagcgg tggtttgttt gccggatcaa    3840
gagctaccaa ctctttttcc gaaggtaact ggcttcagca gagcgcagat accaaatact   3900
gtccttctag tgtagccgta gttaggccac cacttcaaga actctgtagc accgcctaca   3960
tacctcgctc tgctaatcct gttaccagtg gctgctgcca gtggcgataa gtcgtgtctt   4020
accgggttgg actcaagacg atagttaccg gataaggcgc agcggtcggg ctgaacgggg   4080
ggttcgtgca cacagcccag cttggagcga acgacctaca ccgaactgag atacctacag   4140
cgtgagctat gagaaagcgc cacgcttccc gaagggagaa aggcggacag gtatccggta   4200
agcggcaggg tcggaacagg agagcgcacg agggagcttc caggggggaaa cgcctggtat  4260
ctttatagtc ctgtcgggtt tcgccacctc tgacttgagc gtcgattttt gtgatgctcg   4320
tcaggggggc ggagcctatg gaaaaacgcc agcaacgcgg ccttttacg gttcctggcc    4380
ttttgctggc cttttgctca catgttcttt cctgcgttat cccctgattc tgtggataac   4440
cgtattaccg cctttgagtg agctgatacc gctcgccgca gccgaacgac cgagcgcagc   4500
gagtcagtga gcgaggaagc ggaagagcgc ccaatacga accgcctct ccccgcgcgt    4560
tggccgattc attaatgcag cagctgcgcg ctcgctcgct cactgaggcc gcccgggcaa   4620
agcccgggcg tcgggcgacc tttggtcgcc cggcctcagt gagcgagcga gcgcgcagag   4680
agggagtggc caactccatc actagggtt ccttgtagtt aatgattaac cgccatgct    4740
acttatctac gtagccatgc tctaggacat tgattattga ctagtggagt tccgcgttac   4800
ataacttacg gtaaatggcc cgcctggctg accgcccaac gacccccgcc cattgacgtc   4860
aataatgacg tatgttccca tagtaacgcc aatagggact ttccattgac gtcaatgggt   4920
ggagtattta cggtaaactg cccacttggc agtacatcaa gtgtatcata tgccaagtac   4980
gcccccatatt gacgtcaatg acggtaaatg gcccgcctgg cattatgccc agtacatgac   5040
cttatgggac tttcctactt ggcagtacat ctacgtatta gtcatcgcta ttaccatggt   5100
cgaggtgagc cccacgttct gcttcactct ccccatctcc cccccctccc cacccccaat   5160
tttgtattta tttatttttt aattattttg tgcagcgatg ggggcgggg ggggggggg    5220
cgcgcgccag gcggggcggg gcggggcgag gggcggggcg gggcgaggcg gagaggtgcg   5280
gcggcagcca atcagagcgg cgcgctccga aagtttcctt ttatggcgag gcggcggcgg   5340
cggcggcccct ataaaagcg aagcgcgcgg cgggcgggag tcgctgcgcg ctgccttcgc   5400
cccgtgcccc gctccgccgc cgcctcgcgc cgcccgcccc ggctctgact gaccgcgtta   5460
ctaaaacagg taagtccggc ctccgcgccg ggttttggcg cctcccgcgg gcgcccccct   5520
cctcacggcg agcgctgcca cgtcagacga agggcgcagc gagcgtcctg atccttccgc   5580
ccggacgctc aggacagcgg cccgctgctc ataagactcg gccttagaac cccagtatca   5640
gcagaaggac attttaggac gggacttggg tgactctagg cactggtttt ctttccaga    5700
gagcggaaca ggcgaggaaa agtagtccct tctcggcgat tctgcggagg gatctccgtg   5760
gggcggtgaa cgccgatgat gcctctacta accatgttca tgttttcttt ttttttctac   5820
aggtcctggg tgacaacag ggtaccgcca ccaacgatga taaactgtat cgcgcgcgata  5880
gccgccgcc ggatgaaatt aaacagagcg gcggcctgat gccgcgcggc cagagcgaat   5940
attttgatcg cggcacccag atgaacatta acctgtatga tcatgcgcgc ggcacccaga   6000
ccggctttgt gcgccatgat gatggctatg tgagcaccaa aattagcctg cgcagcgcgc   6060
atctggttggg ccagaccatt ctgagcgcc atagcaccta ttatattat gtgattgcga   6120
ccgcgccgaa catgtttaac gtgaacgatg tgctgggcgc gtatagcagc catccggatg   6180
aacaggaagt gagcgcgctg ggcggcattc cgtatagcca gatttatggc tggtatcgcg   6240
tgcattttgg cgtgctggat gaacagctgc atcgcaaccg cggctatcgc gatcgctatt   6300
atagcaacct ggatattgcg ccggcggcgg atggctatgg cctggcgggc tttccgccgg   6360
aacatcgcgc gtggcgcgaa gaaccgtgga ttcatcgcgc gccgcggcc tgcggcaacg    6420
cgccgcgcag cagcatgagc aacacctgcg atgaaaaaac ccagagcctg gccgtgaaat   6480
ttctggatga atatcagagc aaagtgaaac gccagatttt tagcggctat cagagcgata   6540
ttgatcccca taaccgcatt aaaagatgaac tgatggcaac agggagccga acctctctgc   6600
tccttgcttt cgggctcctt tgcctaccgt ggctccaaga gggctcggca accccgcaga   6660
acattaccga tctgtgcgcg gaatatcata acacccgatt tcatacccg aacgataaaa    6720
ttttagcta taccgaaagc ctggcgggca aacgcaaat ggcgattatt acctttaaaa     6780
acggcgcgac ctttcaggtg gaagtgccgg gcagccagca tattgatagc cagaaaaaag   6840
cgattgaacg catgaaagat accctgcgca ttgcgtatct gaccgaagcg aaagtggaaa   6900
aactgtgcgt gtggaacaac aaaacccgc atgcgattgc ggcgattagc atggcgaact    6960
ctagagat                                                                                  6968
```